United States Patent [19]

Rebers et al.

[11] 4,136,169

[45] Jan. 23, 1979

[54] CROSS-PROTECTIVE FOWL CHOLERA BACTERINS

[75] Inventors: Paul A. Rebers, Nevada, Iowa; Kenneth L. Heddleston, Lakeview, Ark.

[73] Assignee: The United States of America, as represented by the Secretary of Agriculture, Washington, D.C.

[21] Appl. No.: 880,832

[22] Filed: Feb. 24, 1978

[51] Int. Cl.² .............................................. A61K 39/02
[52] U.S. Cl. ........................................................ 424/92
[58] Field of Search ........................................... 424/92

[56] References Cited

U.S. PATENT DOCUMENTS

| | | | |
|---|---|---|---|
| 2,787,576 | 4/1957 | Kakavas et al. | 424/92 |
| 3,139,382 | 6/1964 | Killinger | 424/92 |
| 3,328,252 | 6/1967 | Mora | 424/92 |
| 3,855,408 | 12/1974 | Maheswaran | 424/92 |

OTHER PUBLICATIONS

Heddleston Avian Diseases vol. VI, No. 3, pp. 315-321 (1962) Studies on Pasteurellosis. v. Two Immunoganic types of Pasteurella multocida Associated with Fowl Cholera.
Heddleston et al. Avian Diseases vol. IX No. 3, pp. 367-376 (1965) Fowl Chloera; Comparison of Serologic and Immunogenic Responses of Chickens and Turkeys.
Heddleston et al. Avian Diseases vol. 16 No. 3; pp. 578-586 (1972) Fowl Cholera; Cross-Immunity induced in Turkeys with formalin-killed in-vivo Propagated Pasteurella multocida.
Heddleston et al. Avian Diseases vol. 18 No. 2: pp. 213-214 (1974) "Fowl Cholora Bacterins: Host-Specific cross-immunity induced in turkeys with Pasteurella multocida propagated in embryonating turkey eggs".

*Primary Examiner*—Shep K. Rose
*Attorney, Agent, or Firm*—M. Howard Silverstein; David G. McConnell; Curtis P. Ribando

[57] ABSTRACT

Cross-protection of fowl against different serologic and immunologic types of *Pasteurella multocida,* responsible for fowl cholera, has been achieved by a novel process for preparing *P. multocida* bacterins. Bacterial cells from infected fowl tissue are passaged only once through a laboratory medium, sterilized, and recovered for use.

7 Claims, No Drawings

CROSS-PROTECTIVE FOWL CHOLERA BACTERINS

BACKGROUND OF THE INVENTION

1. Field of the Invention

This invention relates to the cross-protection of fowl against different serologic and immunologic types of *Pasteurella multocida* responsible for fowl cholera. In the United States alone, the cost of this disease to the turkey growers in the top 11 turkey-producing states (National Turkey Federation Symposium, University of Minnesota, 1970) amounted to at least $15 million. Although the acute form of the disease causes death in 1–5 days, a small number of infected birds may survive. Survivors are usually debilitated and are potential carriers of the disease.

2. Description of the Prior Art

The conventionl procedure for preparing fowl cholera bacterins is taught by Heddleston, Avian Diseases, Vol. VI, No. 3: 315–321 (1962). The *Pasteurella multocida* organisms are first isolated from infected fowl tissue with the aid of an agar medium. Selected colonies from the agar medium are then grown in tryptose broth medium, and the culture is then lyophilized and stored until use. Cells are grown from a lyophilized culture by the addition of a liquid medium such as tryptose broth, and incubated at 37°. Routinely, the organism is subcultured on agar media to insure purity. To prepare a bacterin, the organism is then killed by addition of a sterilizing solution, such as formalin. The experiments shown in Heddleston, supra, illustrate that bacterins prepared by this procedure adequately protect vaccinated fowl against only the *P. multocida* strain homologous to that of the bacterin. Several experiments designed to test the benefit of enriched laboratory media on the development of better cross-immunizing bacterins have led to very little success. Other experiments by Heddleston illustrate that multivalent bacterins are sometimes effective against multiple strains of the organism, but the practicality of such is diminished by the added expense, the danger of immuno-suppression, and the difficulty in choosing the proper combination of serotypes. At the present time 16 different serotypes of *Pasteurella multocida* have been isolated, but the actual number is probably greater. Moreover, it is shown in Heddleston et al., Avian Diseases, Vol. IX, No. 3: 367–376 (1965) that bacterins containing only one strain of *P. multocida* gave better immunity in turkeys to homologous challenge than the bivalent and trivalent ones.

Cross-protection in turkeys has been achieved by Heddleston et al., Avian Diseases, Vol. 16, No. 3: 578–586 (1972) with fowl cholera bacterins prepared from turkey liver and blood tissue. Infected liver and heart blood was homogenized in a "Waring" blendor with formolized NaCl solution and centrifuged. The supernatant was used as the bacterin. Such a procedure, however, is economically unfeasible for immunizing large numbers of fowl. In this reference, Heddleston also demonstrates inducing cross-immunity in turkeys by administering a live avirulent mutant strain of *P. multocida* in the drinking water. However, the avirulent strain is reported to induce immunity for only a relatively short time, 3–6 weeks, and the live vaccine poses a health hazard for the more susceptible animal.

Some cross-protection was also observed by Heddleston et al., Avian Diseases, Vol. 18, No. 2: 213–219 (1974) by vaccinating turkeys with fowl cholera bacterins prepared from infected embryonating turkey eggs. As with the bacterins prepared from mature turkey tissue, this procedure is economically unfeasible.

SUMMARY OF THE INVENTION

We have now discovered a novel method for preparing modified bacterins useful in the cross-protective vaccination of fowl against strains of both the same and different immunologic and serologic types of *Pasteurella multocida*. We have unexpectedly found that the ability to induce cross-protection is retained by the bacterial cells if they are passaged only once through a laboratory medium prior to killing. Thus, our novel method comprises the following steps:

a. providing fowl tissue infected with cells of a strain of *P. multocida*;
b. inoculating a culture medium with said tissue infected with the *P. multocida* cells;
c. propagating the *P. multocida* cells on the inoculated culture medium;
d. killing the cells propagated on the inoculated medium to yield the modified bacterins; and
e. recovering the modified bacterins from step (d).

In accordance with this method, it is an object of the invention to prepare fowl cholera bacterins which are capable of inducing a broad spectrum of protection and a high degree of immunity.

It is also an object of the invention to prepare fowl cholera bacterins which are safe to handle and incapable of inducing the disease in the vaccinated animals.

Another object of the invention is to prepare a fowl cholera bacterin which is relatively simple and economically feasible to produce.

Other objects and advantages of the invention will become readily apparent from the ensuing description.

DETAILED DESCRIPTION OF THE INVENTION

The term "fowl" is used throughout the disclosure to include any avian animal (i.e., bird), whether wild or domestic, which is susceptible to fowl cholera disease caused by *Pasteurella multocida*, or which is a carrier of the disease. Without limitation thereto, exemplary fowl include chickens, turkeys, geese, ducks, crows, and the like.

*P. multocida* is the bacterium responsible for the fowl cholera disease. Unless otherwise specified, the term will be used throughout the disclosure in the broadest sense to include all immunologic and serologic types and all strains thereof. Strains belonging to the same serologic type are homologous strains and usually belong to the same immunologic type as well. Strains belonging to different serologic types are heterologous.

"Vaccine" is defined herein in its broad sense to mean all types of biological agents used to produce active immunity.

"Bacterin" is used throughout the disclosure to mean a type of vaccine comprising bacterial cells which are killed by chemical or physical means and are capable of inducing active immunity. In administrable form, they are usually prepared as suspensions of the bacterial cells.

"Inoculated culture medium" is defined herein to mean the medium which is directly inoculated with the *P. multocida*-infected fowl tissue, without passage through an intervening laboratory medium.

In the preparation of the novel bacterins of the instant invention, in vivo-propagated *P. multocida* cells are obtained from body tissue of a host bird. The bird is preferably one which has died of acute fowl cholera though tissue may also be obtained from living animals infected with the disease. Any infected tissue, such as from the liver, blood, heart, or spleen would be a suitable source of the bacterial cells. The liver is normally used because of its accessibility and high concentration of *P. multocida* cells.

Though it is not necessary, the infected tissue is preferably converted to a more workable state by dispersing it in solution. Any conventional means such as a "Waring" blendor can be used to homogenize and disperse the tissue. Suitable dispersing media for maintaining bacterial viability are known in the art and do not constitute novelty within the invention. Preferred is an inexpensive and non-nutritive medium such as physiological strength saline (0.15 molar NaCl). Of course, it is understood that other solutes which impart sufficient osmotic pressure to the solution in order to prevent lysing of the bacterial cells could be substituted for the NaCl. Exemplary of these are $Na_2SO_4$, $K_2SO_4$, $MgSO_4$, KCl, $CaCl_2$, sucrose, and glucose.

A culture medium is then directly inoculated with the *P. multocida*-infected tissue. It is preferred to use an agar medium, such as Difco's dextrose-starch-agar. Of course, it is understood that any well-known medium for propagating *P. multocida* can be substituted therefor. The cells may be incubated under any conditions suitable for growth, generally in a temperature range of about 25°–42° C. The optimum incubation temperature is at about 37° C. Incubation periods of at least 6 hours are required for full growth and it is normally preferred to continue incubation for at least 18–24 hours.

After propagation on the originally inoculated culture medium, and without any subsequent subculturing, the *P. multocida* cells are then killed. Any standard technique of sterilizing the bacterial culture can be used without affecting the efficacy of the resultant bacterin. The preferred procedure is to harvest the cultured cells with formolized saline solution. Alternatively, the *P. multocida* could be killed with other agents such as betapropiolactone, phenol, sodium azide, thimerosal, and neomycin, or by other methods including heating and drying.

The bacterins so produced are thereafter recovered and prepared in an administrable form. They are generally suspended in a saline solution or incorporated in a water-in-oil emulsion as well known in the art.

When administered to fowl, the novel modified bacterins induce 80–100% protection against the homologous strain which is comparable to that of the standard prior art bacterins prepared by lyophilizing and subculturing the inoculated culture. Additionally, tests have proven that the novel modified bacterins induce approximately 70% cross-protection against different immunologic and serologic types of *P. multocida*, as compared to 0–40% cross-protection induced by the standard bacterins.

The following examples are intended only to further illustrate the invention and are not intended to limit the scope of the invention which is defined by the claims.

EXAMPLE A

*Pasteurella multocida* strain X-73 (serotype 1) and strain P-1059 (serotype 3), respectfully isolated originally from a chicken and a turkey, were subcultured on agar, lyophilized, and stored at 4° C. When cultures were needed to prepare bacterins or to challenge the immunity of the birds, a part of the lyophilized stock was opened, transferred to tryptose broth, plated on dextrose-starch-agar, and incubated for 18–24 hours at 37° C.

EXAMPLES 1–5

A suspension of *P. multocida* strain P-1059 from Example A was used to swab the nasal clefts of chickens or turkeys. The birds died within 2 days, and their liver and heart blood, hereafter referred to as host tissue, were homogenized in a "Waring" blendor with a buffered salt solution (0.15 molar NaCl containing 0.02 molar phosphate buffer at pH 7.2). The tissue dispersion was used to inoculate dextrose-starch-agar medium. After incubation for 18–24 hours at 37° C., bacterins were prepared by harvesting the cells with saline containing 0.3% formalin (hereafter designated as formolized saline) and adjusting the suspension to a 10 × 1 McFarland density. The bacterin was checked for sterility after 4 days at 22° C. Turkeys were inoculated with 1.0 ml. of the bacterins given subcutaneously in the neck. They were subsequently challenged with 0.1–0.2 ml. of a tryptose broth suspension of organisms given intramuscularly in the thigh. Nicholas Broad-Breasted White turkeys were used in Examples 1 and 3–5. Beltsville Small White turkeys were used for Example 2. The vaccination and challenge schedule and the protection results are given in the table.

EXAMPLES 6–8

The procedure of Examples 1–5 was repeated except that the dextrose-starch-agar medium also contained 5% defibrinated turkey blood, and the bacterin of Example 8 was emulsified with an equal volume of "Bayol F" mineral oil containing 3% "Arlacel A". The test animals were Nicholas Broad-Breasted White turkeys. The vaccination and challenge schedule and the protection results are given in the table.

EXAMPLES 9–13

In Examples 9–13, bacterins were prepared in accordance with the prior art procedures. Lyophilized stock cultures of *P. multocida* strains X-73 and P-1059 as prepared in Example A were suspended in tryptose broth medium and incubated at 37° C. The tryptose broth was then used to inoculate dextrose-starch-agar medium. Typical colonies were selected from the agar, suspended in tryptose broth, incubated, and transferred to dextrose-starch-agar plates. For Example 9, the culture was transferred four more times on dextrose-starch-agar media. Bacterins were prepared by washing the cells off the agar media with formolized saline and held at least 4 days at 22° C., after which they were checked for sterility. The bacterins of Examples 10–13 were emulsified with an equal volume of "Bayol F" mineral oil containing 3% "Arlacel A". The test animals used in Example 9 were Beltsville Small White turkeys, and those used in Examples 10–13 were Nicholas Broad-Breasted White turkeys. The vaccination and challenge schedule and the protection results are given in the table.

EXAMPLES 14–16

As controls, nonvaccinated turkeys were challenged with either *P. multocida* strain X-73 or P-1059. Beltsville Small White turkeys were used for Example 14 and Nicholas Broad-Breasted White turkeys were used for Examples 15 and 16. The challenge schedule and the protection results are given in the table.

The *P. multocida* strains X-73 and P-1059 used in the Examples are deposited in the American Type Culture Collection in Rockville, Maryland and assigned deposit numbers 11039 and 15742, respectively. These strains are well known and widely used by the fowl cholera vaccine industry. A taxonomic description of both is given in *Diseases of Poultry*, 6th Ed., Hofstad et al., Chapter 5.

It is understood that the foregoing detailed description is given merely by way of illustration and that modification and variations may be made therein without departing from the spirit and scope of the invention.

Table

| Example | Age at first vaccination (days) | Age at second vaccination (days) | Age when challenged | Tissue host | Bacterin strain | Challenge strain | S/C[a] | Percent protected |
|---|---|---|---|---|---|---|---|---|
| Novel bacterins | | | | | | | | |
| 1 | 43 | 64 | 79 | turkey | P-1059 | X-73 | 8/10 | 80 |
| 2 | 32 | 41 | 50 | chicken | P-1059 | X-73 | 9/12 | 75 |
| 3 | 29 | 55 | 70 | chicken | P-1059 | X-73 | 7/9 | 78 |
| 4 | 32 | 63 | 79 | chicken | P-1059 | X-73 | 9/15 | 60 |
| 5 | 32 | 63 | 79 | turkey | P-1059 | X-73 | 14/15 | 93 |
| 6 | 44 | 65 | 78 | turkey | P-1059 | X-73 | 8/10 | 80 |
| 7 | 44 | 65 | 78 | turkey | P-1059 | P-1059 | 7/10 | 70 |
| 8 | 44 | 65 | 78 | turkey | P-1059 | X-73 | 7/10 | 70 |
| Prior art bacterins | | | | | | | | |
| 9 | 32 | 41 | 50 | — | P-1059 | X-73 | 1/12 | 8 |
| 10 | 44 | 65 | 78 | — | P-1059 | X-73 | 3/9 | 33 |
| 11 | 44 | 65 | 78 | — | P-1059 | P-1059 | 10/10 | 100 |
| 12 | 44 | 65 | 78 | — | X-73 | X-73 | 10/10 | 100 |
| 13 | 44 | 65 | 78 | — | X-73 | P-1059 | 4/9 | 44 |
| Controls | | | | | | | | |
| 14 | — | — | 50 | — | | X-73 | 0/13 | 0 |
| 15 | — | — | 78 | — | | X-73 | 0/10 | 0 |
| 16 | — | — | 78 | — | | P-1059 | 0/10 | 0 |

[a]Number of survivors 2 weeks after challenge, versus total number challenged.

We claim:

1. A method for preparing modified bacterins useful in the cross-protective vaccination of fowl against strains of both the same and different immunologic and serologic types of *Pasteurella multocida* comprising the following steps:

a. providing fowl tissue infected with cells of a strain of said *Pasteurella multocida*;
   b. inoculating a culture medium with said tissue infected with said *Pasteurella multocida* cells;
   c. passaging said *Pasteurella multocida* cells on said inoculated culture medium; only once, without subsequent sub-culturing
   d. killing said cells passaged on said inoculated medium to yield said modified bacterins; and
   e. recovering said modified bacterins from step (d).

2. The method as described in claim 1 wherein said fowl tissue in step (a) is provided from a turkey.

3. The method as described in claim 1 wherein said fowl tissue in step (a) is provided from a chicken.

4. The method as described in claim 1 wherein said fowl tissue in step (a) is dispersed in a salt solution.

5. The method as described in claim 1 wherein said strain of *Pasteurella multocida* in step (a) is X-73.

6. The method as described in claim 1 wherein said strain of *Pasteurella multocida* in step (a) is P-1059.

7. The method as described in claim 1 wherein said culture medium in step (b) is dextrose-starch-agar.

* * * * *